(12) United States Patent
Maas et al.

(10) Patent No.: US 6,906,230 B1
(45) Date of Patent: Jun. 14, 2005

(54) METHOD FOR PRODUCING ALCOHOL SURFACTANTS AND ALCOHOL ETHER SURFACTANTS, THE PRODUCTS OBTAINED AND THEIR USE

(75) Inventors: Heiko Maas, Schifferstadt (DE); Michael Röper, Wachenheim (DE); Marc Walter, Frankenthal (DE); Ralf Schulz, Speyer (DE); Jürgen Tropsch, Römerberg (DE); Hans-Ulrich Jäger, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,168

(22) PCT Filed: Mar. 17, 2000

(86) PCT No.: PCT/EP00/02416

§ 371 (c)(1),
(2), (4) Date: Sep. 18, 2001

(87) PCT Pub. No.: WO00/56683

PCT Pub. Date: Sep. 28, 2000

(30) Foreign Application Priority Data

Mar. 19, 1999 (DE) ......................... 199 12 418

(51) Int. Cl.$^7$ ................... C07C 29/36; C07C 29/38; C07C 29/40; C07C 29/44; C07C 29/46
(52) U.S. Cl. ................. 568/909; 568/613; 568/622; 585/511; 585/512; 585/502; 585/545; 562/94
(58) Field of Search ................... 568/909, 613, 568/622; 585/511, 512, 502, 545; 562/94

(56) References Cited

U.S. PATENT DOCUMENTS

| | | | |
|---|---|---|---|
| 3,179,710 A | | 4/1965 | Ratajczak et al. |
| 3,315,009 A | * | 4/1967 | Engelbrecht et al. .. 260/683.15 |
| 3,317,628 A | | 5/1967 | Schuck et al. |
| 3,420,875 A | | 1/1969 | Di Salvo et al. |
| 3,462,525 A | | 8/1969 | Levinsky et al. |
| 3,524,864 A | | 8/1970 | Rubinfeld et al. |
| 4,069,273 A | | 1/1978 | Komoto |
| 4,959,491 A | * | 9/1990 | Threlkel ...................... 562/94 |
| 5,780,694 A | | 7/1998 | Singleton |
| 5,849,972 A | | 12/1998 | Vicari et al. |

FOREIGN PATENT DOCUMENTS

| | | |
|---|---|---|
| DE | 43 39 713 | 5/1995 |
| DE | 196 04 466 | 8/1997 |
| EP | 0 787 704 | 8/1997 |
| FR | 964.922 | 8/1950 |
| FR | 1.274.529 | 9/1961 |
| FR | 1.403.273 | 5/1965 |
| GB | 1 471 481 | 4/1977 |
| WO | WO 97/16398 | 5/1997 |
| WO | WO 97/38957 | 10/1997 |
| WO | WO 98/23566 | 6/1998 |

OTHER PUBLICATIONS

K. Kosswig, et al., Kapitel 23, Carl Hanser Verlag Muenchen Wien, pp. 145–161, "Die Tenside", 1993.
K. Weissermel, et al., Industrielle Organische Chemie, pp. 94–98, "Olefin Metathesis", 1997 (with English translation, pp. 85–89).
M. Beller, et al., Journal of Molecular Catalysis, vol. 104, pp. 17–85, "Progress in Hydroformylation and Carbonylation", 1995.
W. Bertleff, Ullmann's Encyclopedia of Industrial Chemistry, vol. A5, pp. 217–234 and 331–334, "Carbonylation", 1986.
W. Bertleff, Ullmann's Encyclopedia of Industrial Chemistry, vol. A5, pp. 331–334, "Catalysis and Catalysts", 1986.
B. Elvers, et al., Comils/Hermannl., Ullmann's Encyclopedia of Industrial Chemistry, vol. A13 and A18, "High–Performance Fibers to Imidazole and Derivatives", 1990/1991.
A. J. Kresge, et al., Journal of the American Chemical Society, vol. 93, No. 19, pp. 4907–4908, "General Acid Catalysis in the Hydration of Simple Olefins. The Mechanism of Olefin Hydration", Sep. 22, 1971.
E. Muller, et al., Houben–Weyl, vol. V/4, pp. 102–132 and 535–539, "Methoden Der Organischen Chemie", 1960.
N. Jones, et al., Journal of the Chemical Society, pp. 1345–1347, "Aliphatic Friedel–Crafts Reactions. part IV. The Preparation of Divinyl Ketones", 1961.
B. Wojtech, Die Macromoleculare Chemie, vol. 66, pp. 180–195, "Zur Darstellung Hochmolekularer Polyaethylenoxyde", 1963.
P. H. Plech, Ullmann's Encyclopedia of Industrial Chemistry, Plastics, Properties and Testing to Polyvinyl Compounds, vol. A 21, pp. 583–584, "Polyoxyalkylenes", 1963.
Barbara Elvers, et al., Ullmann's Encyclopedia of Industrial Chemistry, vol. A 25, pp. 779–783 and 792–793, "Surfactants", 1994.
K. Igarashi, et al.; Advances in Carbohydrate Chemistry and Biochemistry, vol. 34; pp. 243–283, "The Koenigs–Knorr Reaction", 1977.
G. Wullf, et al., Angewandte Chemie, vol. 86, No. 5, pp. 173–187, "Ergebnisse Und Probleme Der O–Glykosidsynthese", 1974.
H. Krauch, et al., Reaktionen der Organischen Chemie, pp. 404–409, "Ein Beitrag Zur Terminologie Der Organischen Chemie", 1976.
F. Ramirez, et al., Synthesis, pp. 449–488, "Synthesis of Phosphodiesters: The Cyclic Enediol Phosphoryl (CEP) Method", 1985.
Ullmann's Encyclopedia of Industrial Chemistry, 5$^{th}$ Ed., vol. A21, p. 502.
Ullmann's Encyclopedia of Industrial Chemistry, 5$^{th}$ Ed., vol. A18, p. 231.
Ullmann's Encyclopedia of Industrial Chemistry, 6$^{th}$ Ed., vol. 17, p. 22.
Ullmann's Encyclopedia of Industrial Chemistry, 5$^{th}$ Ed., vol. A5, pp. 326–327.
Ullmann's Encyclopedia of Industrial Chemistry, 6$^{th}$ Ed., vol. 16, pp. 327–328, Chapter 2.2.
Ullmann's Encyclopedia of Industrial Chemistry, 6$^{th}$ Ed., vol. 16, pp. 322–328.
Ullmann's Encyclopedia of Industrial Chemistry, 5$^{th}$ Ed., vol. A18, p. 227.

* cited by examiner

*Primary Examiner*—Elvis O. Price
(74) *Attorney, Agent, or Firm*—Oblon, Spivak, McClelland, Maier & Neustadt, P.C.

(57) ABSTRACT

The invention describes a process for the preparation of surfactant alcohols and surfactant alcohol ethers which are, inter alia, highly suitable as surfactants or for the preparation of surfactants. The process, starting from olefin mixtures having a defined minimum content of linear hexenes, gives mixtures having a predominant fraction of branched dodecenes, which are subsequently derivatized to give surfactant alcohols and then optionally alkoxylated.

The surfactant alcohol mixture obtained in the process has a degree of branching of from 2.0 to 3.0 and in particular exhibits advantageous properties as regards ecotoxicity and biodegradability.

A description is also given of the use of the surfactant alcohols and surfactant alcohol ethers as surfactants by glycosidation or polyglycosidation, sulfation or phosphation.

4 Claims, No Drawings

METHOD FOR PRODUCING ALCOHOL SURFACTANTS AND ALCOHOL ETHER SURFACTANTS, THE PRODUCTS OBTAINED AND THEIR USE

The present invention relates to a process for the preparation of surfactant alcohols and surfactant alcohol ethers which, inter alia, are highly suitable as surfactants or for the preparation of surfactants. The process, starting from olefin mixtures having a defined minimum content of linear hexenes, produces mixtures having a predominant fraction of branched dodecenes, which are subsequently derivatized to give surfactant alcohols and then optionally alkoxylated.

The invention further relates to the use of the surfactant alcohols and surfactant alcohol ethers for the preparation of surfactants by glycosidation or polyglycosidation, sulfation or phosphation.

Fatty alcohols having chain lengths from $C_8$ to $C_{18}$ is are used for the preparation of nonionic surfactants, They are reacted with alkylene oxides to give the corresponding fatty alcohol ethoxylates. (Chapter 2.3 in: Kosswig/Stache,"Die Tenside" [Surfactants], Carl Hanser Verlag, Munich Vienna (1993)). The chain length of the fatty alcohol influences various surfactant properties, such as, for example, wetting ability, foam formation, ability to dissolve grease, cleaning power.

Fatty alcohols having chain lengths from $C_8$ to $C_{18}$ can also be used for preparing anionic surfactants, such as alkyl phosphates and alkyl ether phosphates. Instead of phosphates, it is also possible to prepare the corresponding sulfates. (Chapter 2.2. in: Kosswig/Stache"Die Tenside" [Syrfactants], Carl Ilanser Verlag, Munich Vienna (1993)).

Such fatty alcohols are obtainable from native sources, e.g. from fats and oils, or else in a synthetic manner by construction from building blocks having a lower number of carbon atoms. One variant here is the dimerization of an olefin to give a product having twice the number of carbon atoms and its functionalization to give an alcohol.

Linear olefins of suitable chain length are currently accessible mainly by two processes:

In the Fischer-Tropsch synthesis, as well as paraffins, olefin isomer mixtures form as coupling products.

The oligomerization of ethylene has established itself as a further source for obtaining suitable olefins on an industrial scale. In this process, the catalysts used are alkylaluminums and also homogeneous nickel catalysts, as in the case of the known SHOP process from Shell (Weissermel/Arpe, Industrielle organische Chemie [Industrial Organic Chemistry]).

Olefin fractions of suitable chain length are further processed to give surfactant alcohols. The use of ethylene has the disadvantage of high feed material costs for the monomer building block. Processes for the preparation of surfactants which are based on ethylene as starting material are therefore important economically.

For the, dimerization of olefins, a number of processes are known. For example, the reaction can be carried out over a heterogeneous cobalt oxide/carbon catalyst (FR-A-1 403 273), in the presence of acids such as sulfuric or phosphoric acid (FR 964 922), with an alkylaluminum catalyst (WO 97/16398), or with a homogeneously dissolved nickel complex catalyst (U.S. Pat. No. 4 069 273). According to the details in U.S. Pat. No. 4,069,273, the use of these nickel complex catalysts (the complexing agent used being 1,5-cyclooctadiene or 1,1,1,5,5,5-hexafluoropentane-2,4-dione) gives highly linear olefins with a high proportion of dimerization products.

FR-A-1 274 529 describes the Lewis-acid-catalyzed dimerization of methylpentenes, where the Lewis acid used is boron trifluoride. This process has the disadvantage that it is difficult to separate off the catalyst from the reaction product. As a result, not only are products contaminated with catalyst residues obtained, but the catalyst loss is also considerable.

Functionalization of the olefins to give alcohols with extension of the carbon skeleton about a carbon atom advantageously takes place via the hydroformylation reaction, which gives a mixture of aldehydes and alcohols, which can then be hydrogenated to give alcohols. Approximately 7 million metric tons of products per annum are produced worldwide using the hydroforrnylation of olefins. An overview of catalysts and reaction conditions for the hydroformylation process is given, for example, by Belier et al. in Journal of Molecular Catalysis, A104 (1995), 17–85 and also in Ullmann's Encyclopedia of Industrial Chemistry, vol. A5 (1986), page 217 et seq., page 333, and the relevant literature references.

From WO 98/23566 it is known that sulfates, alkoxylates, alkoxysulfates and carboxylates of a mixture of branched alkanols (oxo alcohols) exhibit good surface activity in cold water and have good biodegradability. The alkanols in the mixture used have a chain length of greater than 8 carbon atoms, having on average from 0.7 to 3 branches. The alkanol mixture can be prepared, for example by hydroformylation, from mixtures of branched olefins which for their part can be obtained either by skeletal isomerization or by dimerization of internal, linear olefins.

A given advantage of the process is that no $C_3$- or $C_4$-olefin stream is used for the preparation of the dimerization feed. It follows from this that, according to the current prior art, the olefins subjected to dimerization therein must have been prepared from ethylene (e.g. SHOP process). Since ethylene is a relatively expensive starting material for surfactant manufacture, ethylene-based processes have a disadvantage in terms of cost compared with processes which start from $C_3$- and/or $C_4$-olefin streams.

The structure of the components of the oxo alkanol mixture depends .on the type of olefin mixture which has been subjected to hydroformylation. Olefin mixtures which have been obtained by skeletal isomerization from alpha-olefin mixtures lead to alkanols which are branched predominantly at the ends of the main chain, i.e. in positions 2 and 3, calculated from the end of the chain in each case.

The surface-active end products are obtained from the alkanol mixtures either by oxidation of the —CH$_2$OH group to give the carboxyl group, or by sulfation of the alkanols or their alkoxylates.

Similar processes for the preparation of surfactants are described in the PCT Patent Application WO 97/38957 and in EP-A-787 704. Also in the processes described therein, an alpha-olefin is dimerized to give a mixture of predominantly vinylidene-branched olefin dimers:

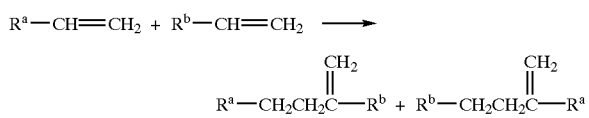

The vinylidene compounds are then double-bond-isomerized, such that the double bond migrates from the end of the chain further into the center, and are then subjected to hydroformylation to give an oxo alcohol mixture. The latter is then further reacted, e.g. by sulfation to give surfactants. A serious disadvantage of this process is that it starts from alpha-olefins. Alpha-olefins are obtained, for example, by transition-metal-catalyzed oligomerization of ethylene, Ziegler build-up reaction, wax cracking or Fischer-Tropsch processes and are therefore relatively expensive starting materials for the manufacture of surfactants. A further considerable disadvantage of this known surfactant preparation process is that a skeletal isomerization must be inserted in the process between the dimerization of the alpha-olefins and the hydroformylation of the dimerization product if predominantly branched products are desired. Because it uses a starting material which is relatively expensive for surfactant manufacture and because of the need to insert an additional process step, the isomerization, this known process is at a considerable disadvantage in terms of cost.

U.S. Pat. No. 5,780,694 describes the preparation and use of alcohols having degrees of branching between 0.9 and 2. The alcohols are prepared by homogeneously catalyzed dimerization of internal olefins and subsequent hydroforrnylation, where the n-proportion in the olefin to be dimerized is more than 85% by weight. A particular advantage of these alcohols is given as the cold washing behavior of their sulfates. Information about the properties of the corresponding ethoxylates and sulfates thereof is not given in this publication. A further advantage of this process is given as being the fact that, for the preparation of the alcohols, no propene- or butene-containing olefin mixtures are used, but mixtures which comprise at least 85% by weight of $C_6$- to $C_{10}$-olefins.

In the parallel German patent application 198 59 911.0, the preparation of tridecanol mixtures by dimerization of so-called "dimer propene" and subsequent hydroformylation of the dodecene mixture is described. It typically comprises less than 30% by weight of linear hexenes. The "dimer propene" used in this process is a hexene isomer mixture which is produced in refinery processes during the oligomerization of propene, e.g. by the ®DIMERSOL process (cf Cornils/Herrrnann, Applied Homogeneous Catalysis, Verlag Chemie (1996)).

Other suitable starting materials for this process are olefin mixtures which are prepared by dimerization of C3/C4 cuts or C4 fractions, e.g. by the DIMERSOL process. The relation between ecotoxicity and biodegradability of the alkanol mixtures prepared is, however, still not optimal.

From the discussed disadvantages of the prior art, in particular also from the need to reduce the preparation costs, arises the object of providing a process for the preparation of surfactant alcohols which are advantageous in termns of application, in which the use of expensive raw materials, in particular costly ethylene, can be avoided.

Surprisingly, we have now found that branched olefins and alcohols (oxo alcohols), which can be further processed to give very highly effective surfactants—referred to below as "surfactant alcohols"—and which have an advantageous combination of favorable properties as regards their preparation and further processing and in particular with regard to their ecotoxicity and biodegradability, can be obtained if the process is carried out according to the invention as described below.

This invention relates to a process for the preparation of surfactant alcohols which have particularly advantageous properties with regard to ecotoxicity and biodegradability and of corresponding surfactant alcohol ethers by a) dimerization of olefin mixtures,
b) derivatization to give primary alcohols, and
c) optional subsequent alkoxylation, which comprises using an olefin mixture which comprises from 30 to 80% by weight of linear hexene isomers and overall at least 60% by weight of hexene isomers.

The olefin mixture used for the process according to the invention must therefore satisfy two prerequisites:
1. the sum of all hexene isomers present therein, i.e. linear and branched hexene isomers, must be at least 60% by weight, and
2. the sum of the linear hexene isomers present therein must be from 30 to 80% by weight.

It has been found that products with very favorable overall properties can be obtained by the process according to the invention in a particularly economical manner when an olefin mixture is used which is obtained by mixing dimer propene and linear hexenes in the weight ratio from 0.3:1 to 1:0.1.

For use in the process according to the invention, particular preference is given to an olefin mixture consisting of a mixture of dimer propene and linear hexenes in the weight ratio from 0.5:1 to 1:0.5.

In the dimerization of hexene isomer mixtures (step a) of the process according to the invention, dimerization products are obtained which, with regard to further processing to surfactant alcohols, have particularly favorable components and a iw particularly advantageous composition when a dimerization catalyst is used which comprises at least one element of subgroup VIII of the Periodic Table and the catalyst composition and the reaction conditions are chosen such that a dimer mixture is obtained which comprises less than 10% by weight of compounds which have a structural element of the formula I (vinylidene group)

(I)

in which $A^1$ and $A^2$ are aliphatic hydrocarbon radicals.

The dimerization can be carried out with homogeneous or heterogeneous catalysis. Preference is given to the heterogeneous procedure since with this, on the one hand, catalyst removal is simplified, making the process more economical, and on the other hand no waste. waters injurious to the environment are produced, as usually form during the removal of dissolved catalysts, for example by hydrolysis.

Another advantage of the heterogeneous process is that the dirnerization product does not contain halogens, in particular chlorine or fluorine. Homogeneously soluble catalysts generally contain halide-containing ligands or are used in combination with halogen-containing cocatalysts. From such catalyst systems, halogen can be incorporated into the dimerization products, which considerably adversely affects both product quality and further processing, in particular hydroformylation to give surfactant alcohols.

For the heterogeneous catalysis, use is advantageously made of combinations of oxides of metals of subgroup VII with aluminum oxide on support materials made from silicon and titanium oxides, as are known, for example, from DE-A-43 39 713. The heterogeneous catalyst can be used in a fixed bed—then preferably in coarsely particulate form as 1 to 1.5 mm chips—or in suspended form (particle size 0.05 to 0.5 mm). In the case of a heterogeneous procedure, the dimerization is advantageously carried out at temperatures of from 80 to 200° C., preferably from 100 to 180° C., at the pressure prevailing at the reaction temperature, optionally also under a protective gas at a pressure above atmospheric, in a closed system. To achieve optimal conversions, the reaction mixture is advantageously circulated repeatedly, a certain proportion of the circulating product being continuously bled out of the system and replaced by starting material.

In the dimerization according to the invention, mixtures of monounsaturated hydrocarbons are obtained whose components predominantly have a chain length twice that of the starting olefins.

The dimerization catalysts and the reaction conditions are expediently chosen within the framework of the above details such that the olefin mixtures prepared according to the invention comprise a high proportion—as a rule greater than 85%, in particular greater than 90%—of components with branches, and a low proportion as a rule below 15, in particular below 10%—of unbranched olefins. A further characteristic is that predominantly groups having (y-4) and (y-5) carbon atoms are bonded to the branching sites of the main chain, where y is the number of carbon atoms in the dimerized monomer. The value (y-5)=0 means that no side chains are present.

Accordingly, in $C_{12}$-olefin mixtures prepared according to the invention, the main chain preferably carries methyl or ethyl groups at the branching points.

It has also been found that the dimerization mixtures can be further derivatized particularly well when the position of the double bond satisfies certain requirements. In these advantageous olefin mixtures, the position of the double bonds relative to the branches is characterized in that the ratio of "aliphatic" hydrogen atoms to "olefinic" hydrogen atoms is in the range
$H_{aliph.}:H_{olefin.}=47:1$ to $11:1$.

"Aliphatic" hydrogen atoms are those which are bonded to carbon atoms which do not participate in a C=C double bond (πbonding), and "olefinic" hydrogen atoms are those bonded to a carbon atom which participates in a n bond.

Particular preference is given to dimerization mixtures in which the ratio
$H_{aliph.}:H_{olefin.}=23:1$ to $14:1$.

The novel olefin mixtures obtainable by the first step of the process according to the invention and having the structural features given above are likewise provided by the present invention. They are useful intermediates, in particular for the further steps of the process according to the invention, namely the preparation, described below, of branched primary alcohols and surfactants, but can also be used as starting materials in other industrial processes which start from olefins, particularly when the end products are to have improved biodegradability.

If the olefin mixtures according to the invention are to be used for the preparation of surfactants, then they are firstly derivatized in accordance with step b) of the process according to the invention by processes known per se to give surfactant alcohols.

This can be achieved in a variety of ways, which either include the direct or indirect addition of water (hydration) to the double bond, or an addition of CO and hydrogen (hydroformylation) to the C=C double bond.

Hydration of the olefins resulting from process step a) is advantageously carried out by direct water addition with proton catalysis. An indirect route, for example via the addition of high-percentage sulfiric acid to give an alkanol sulfonate and subsequent hydrolysis to give the alkanol, is, of course, also possible. The more advantageous direct water addition is carried out in the presence of acidic, in particular heterogeneous, catalysts and generally at a very high olefin partial pressure and at very low temperatures. Suitable catalysts have proven to be, in particular, phosphoric acid on supports such as, for example, $SiO_2$ or Celite, or else acidic ion exchangers. The choice of conditions depends on the reactivity of the olefins to be reacted and can routinely be ascertained by preliminary experiments (lit.: e.g. A. J. Kresge et al. J. Am. Chem. Soc. 93, 4907 (1971); Houben-Weyl vol. 5/4 (1960), pages 102–132 and 535–539). Hydration generally leads to mixtures of primary and secondary alkanols, in which the secondary alkanols predominate.

For the preparation of surfactants, it is more favorable to start from primary alkanols. It is therefore preferable to effect derivatization—step b) of the process according to the invention—of the olefin mixtures obtained from step a) by reaction of same with carbon monoxide and hydrogen in the presence of suitable, preferably cobalt- or rhodium-containing, catalysts to give branched primary alcohols. (Hydroformylation).

A further preferred subject-matter of the present invention is therefore a process for the preparation of mixtures of primary alkanols which are suitable, inter alia, for further processing to surfactants, by hydrofonnylation of olefins, which comprises using the above-described olefin mixtures according to the invention as starting material.

A good overview of the process of hydroformylation with numerous other literature references can be found, for example, in the extensive article by Beller et al. in Journal of Molecular Catalysis, A104 (1995) 17–85 or in Ullmann's Encyclopedia of Industrial Chemistry, vol. A5 (1986), page 217 et seq., page 333, and the relevant literature references.

The comprehensive information given therein allows the person skilled in the art to hydrofornylate even the branched olefins according to the invention. In this reaction, CO and hydrogen are added to olefinic double bonds, giving mixtures of aldehydes and alkanols according to the following reaction equation:

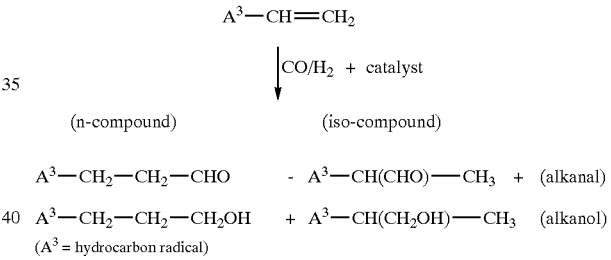

$A^3$—CH=CH$_2$ $\downarrow$ CO/H$_2$ + catalyst (n-compound)    (iso-compound)

$A^3$—CH$_2$—CH$_2$—CHO    -    $A^3$—CH(CHO)—CH$_3$ +    (alkanal)

$A^3$—CH$_2$—CH$_2$—CH$_2$OH    +    $A^3$—CH(CH$_2$OH)—CH$_3$    (alkanol)

($A^3$ = hydrocarbon radical)

The molar ratio of n- and iso-compounds in the reaction mixture is usually in the range from 1:1 to 20:1 depending on the hydroformylation process conditions chosen and the catalyst used. The hydrofonnylation is normally carried out in the temperature range from 90 to 200° and at a CO/H$_2$ pressure of from 2.5 to 35 MPa (25 to 350 bar). The mixing ratio of carbon monoxide to hydrogen depends on whether the intention is to produce alkanals or alkanols in preference. The CO:H$_2$ ratio is advantageously from 10:1 to 1:10, preferably from 3:1 to 1:3, where, for the preparation of alkanals, the range of low hydrogen partial pressures is chosen, and for the preparation of alkanols the range of high hydrogen partial pressures is chosen, e.g. CO:H$_2$=1:2.

Suitable catalysts are mainly metal compounds of the formula HM(CO)$_4$ or M$_2$(CO)$_8$, where M is a metal atom, preferably a cobalt, rhodium or ruthenium atom.

Generally, under hydroformylation conditions, the catalysts or catalyst precursors used in each case form catalytically active species of the formula $H_xM_y(CO)_zL_q$, in which M is a metal of subgroup VIII, L is a ligand, which can be a phosphine, phosphite, amine, pyridine or any other donor compound, including in polymeric form, and q, x, y and z are integers depending on the valency and type of metal, and the covalence of the ligand L, where q can also be 0.

The metal M is preferably cobalt, ruthenium, rhodium, palladium, platinum, osmium or iridium and in particular cobalt, rhodium or ruthenium.

Suitable rhodium compounds or complexes are, for example, rhodium(II) and rhodium(III) salts, such as rhodium(III) chloride, rhodium(II) nitrate, rhodium(III) sulfate, potassium rhodium sulfate, rhodium(II) or rhodium (III) carboxylate, rhodium(II) and rhodium(III) acetate, rhodium (III) oxide, salts of rhodium(III) acid, such as, for example, trisamrnonium hexachlororhodate(III). Also suitable are rhodium complexes such as rhodium biscarbonylacetylacetonate, acetylacetonatobisethylenerhodium(I). Preference is given to using rhodium biscarbonylacetylacetonate or rhodium acetate.

Suitable cobalt compounds are, for example, cobalt(II) chloride, cobalt(II) sulfate, cobalt(II) carbonate, cobalt(II) nitrate, their amine or hydrate complexes, cobalt carboxylates, such as cobalt acetate, cobalt ethylhexanoate, cobalt naphthenate, and the cobalt caprolactamate complex. Here, too, it is possible to use the carbonyl complexes of cobalt, such as dicobalt octacarbonyl, tetracobalt dodecacarbonyl and hexacobalt hexadecacarbonyl.

Said compounds of cobalt, rhodium and ruthenium are known in principle and are described adequately in the literature, or they can be prepared by the person skilled in the art in a manner analogous to that for compounds already known.

The hydroformylation can be carried out with the addition of inert solvents or diluents or without such an addition. Suitable inert additives are, for example, acetone, methyl ethyl ketone, cyclohexanone, toluene, xylene, chlorobenzene, methylene chloride, hexane, petroleum ether, acetonitrile, and the high-boiling fractions from the hydroformylation of the dimerization products.

If the resulting hydroformylation product has too high an aldehyde content, this can be removed in a simple manner by hydrogenation, for example using hydrogen in the presence of Raney nickel or using other catalysts known for hydrogenation reactions, in particular catalysts containing copper, zinc, cobalt, nickel, molybdenum, zirconium or titanium. In the process, the aldehyde fractions are largely hydrogenated to give alkanols. A virtually residue-free removal of aldehyde fractions from the reaction mixture can, if desired, be achieved by posthydrogenation, for example under particularly mild and economical conditions using an alkali metal borohydride.

The mixtures of branched primary alkanols, preparable by hydroformylation of the olefin mixtures according to the invention, are likewise provided by the present invention.

Nonionic or anionic surfactants can be prepared from the alkanols according to the invention in different ways.

Nonionic surfactants are obtained by reacting the alkanols with alkylene oxides (alkoxylation) of the formula II

(II)

in which $R^1$ is hydrogen or a straight-chain or branched aliphatic radical of the formula $C_nH_{2n+1}$, and n is a number from 1 to 16, preferably from 1 to 8. In particular, $R^1$ is hydrogen, methyl or ethyl.

The alkanols according to the invention can be reacted with a single alkylene oxide species or with two or more different species. The reaction of the alkanols with the alkylene oxides forms compounds which in turn carry an OH group and can therefore react afresh with one molecule of alkylene oxide. Therefore, depending on the molar ratio of alkanol to alkylene oxide, reaction products are obtained which have polyether chains of varying length. The polyether chains can contain from 1 to about 200 alkylene oxide structural groups. Preference is given to compounds whose polyether chains contain from 1 to 10 alkylene oxide structural groups.

The chains can consist of identical chain members, or they can have different alkylene oxide structural groups which differ from one another by virtue of their radical $R^1$. These various structural groups can be present within the chain in random distribution or in the form of blocks.

The reaction equation below serves to illustrate the alkoxylation of the alkanols according to the invention using, as example, a reaction with two different alkylene oxides which are used in varying molar amounts x and y.

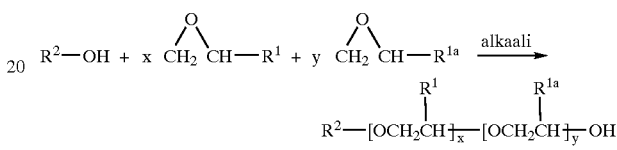

$R^1$ and $R^{1a}$ are different radicals within the scope of the definitions given for $R^1$, and $R^2$—OH is a branched alkanol according to the invention.

The alkoxylation is preferably catalyzed by strong bases, which are advantageously added in the form of an alkali metal hydroxide or alkaline earth metal hydroxide, usually in an amount of from 0.1 to 1% by weight, based on the amount of the alkanol $R^2$—OH (cf. G. Gee et al., J. Chem. Soc. (1961), p. 1345; B. Wojtech, Makromol. Chem. 66, (1966), p. 180).

Acidic catalysis of the addition reaction is also possible. As well as Bronsted acids, Lewis acids, such as, for exarnple, $AlCl_3$ or $BF_3$, are also suitable (cf P. H. Plesch, The Chemistry of Cationic Polymerization, Pergarnon Press, New York (1963)).

The addition reaction is carried out at temperatures of from about 120 to about 220° C., preferably from 140 to 160° C., in a sealed vessel. The alkylene oxide or the mixture of different alkylene oxides is introduced into the mixture of alkanol mixture according to the invention and alkali under the vapor pressure of the alkylene oxide mixture prevailing at the chosen reaction temperature. If desired, the alkylene oxide can be diluted by up to about 30 to 60% using an inert gas. This leads to additional security against explosive polyaddition of the alkylene oxide. If an alkylene oxide mixture is used, then polyether chains are formed in which the various alkylene oxide building blocks are distributed in a virtually random manner. Variations in the distribution of the building blocks along the polyether chain arise due to varying reaction rates of the components and can also be achieved arbitrarily by continuous introduction of an alkylene oxide mixture of a program-controlled composition. If the various alkylene oxides are reacted successively, then polyether chains having block-like distribution of the alkylene oxide building blocks are obtained.

The length of the polyether chains varies within the reaction product in a random manner about a mean, which essentially corresponds to the stoichiometric value arising from the amount added.

The alkoxylates preparable starting from alkanol mixtures and olefin mixtures according to the invention are likewise provided by the present invention. They exhibit very good surface activity and can therefore be used as neutral surfactants in many areas of application.

Starting from the alkanol mixtures according to the invention, it is also possible to prepare surface-active glycosides and polyglycosides (oligoglycosides). These substances too have very good surfactant properties. They are obtained by single or multiple reaction (glycosidation, polyglycosidation) of the alkanol mixtures according to the invention with mono-, di- or polysaccharides with the exclusion of water and with acid catalysis. Suitable acids are, for example, HCl or $H_2SO_4$. As a rule, the process produces oligoglycosides having random chain length distribution, the average degree of oligomerization being from 1 to 3 saccharide radicals.

In another standard synthesis, the saccharide is firstly acetalated with acid catalysis with a low molecular weight alkanol, e.g. butanol, to give butanol glycoside. This reaction can also be carried out with aqueous solutions of the saccharide. The lower alkanol glycoside, for example butanol glycoside, is then reacted with the alkanol mixtures according to the invention to give the desired glycosides according to the invention. After the acidic catalyst has been neutralized, excess long-chain and short-chain alkanols can be removed froni the equilibrium mixture, e.g. by distillation under reduced pressure.

Another standard method proceeds via the O-acetyl compounds of saccharides. The latter are converted, using hydrogen halide preferably dissolved in glacial acetic acid, into the corresponding O-acetylhalosaccharides, which react in the presence of acid-binding agents with the alkanols to give the acetylated glycosides.

Preferred for the glycosidation of the alkanol mixtures according to the invention are monosaccharides, either hexoses, such as glucose, fructose, galactose, mannose, or pentoses, such as arabinose, xylose or ribose. Particular preference for glycosidation of the alkanol mixtures according to the invention is glucose. It is, of course, also possible to use mixtures of said saccharides for the glycosidation. Glycosides having randomly distributed sugar: radicals are obtained, depending on the reaction conditions. The glycosidation can also take place several times, resulting in polyglycoside chains being added to the hydroxyl groups of the alkanols. In a polyglycosidation using different saccharides, the saccharide building blocks can be randomly distributed within the chain or form blocks of the same structural groups.

Depending on the reaction temperature chosen, furanose or pyranose structures can be obtained. To improve the solubility ratios, the reaction can also be carried out in suitable solvents or diluents.

Standard processes and suitable reaction conditions have been described in various publications, for example in "Ullmann's Encyclopedia of Industrial Chemistry", 5th edition vol. A25 (1994), pages 792–793 and in the literature references given therein, by K. Igarashi, Adv. Carbohydr. Chem. Biochem. 34, (1977), pp. 243–283, by Wulff and Rdhle, Angew. Chem. 86, (1974), pp. 173–187, or in Krauch and Kunz, Reaktionen der organischen Chemie [Reactions in Organic Chemistry], pp. 405–408, Huithig, Heidelberg, (1976).

The glycosides and polyglycosides (oligoglycosides) preparable starting from alkanol mixtures and olefin mixtures according to the invention are likewise provided by the present invention.

Both the alkanol mixtures according to the invention and the polyethers prepared therefrom can be converted into anionic surfactants by esterifying (sulfating) them in a manner known per se with sulfiric acid or sulfuric acid derivatives to give acidic alkyl sulfates or alkyl ether sulfates, or with phosphoric acid or its derivatives to give acidic alkyl phosphates or alkyl ether phosphates.

Sulfating reactions of alcohols have already been described, e.g. in U.S. Pat. No. 3,462,525, 3,420,875 or 3,524,864. Details on carrying out this reaction can also be found in "Ullmann's Encyclopedia of Industrial Chemistry", 5th edition vol. A25 (1994), pages 779–783 and in the literature references given therein.

If sulfiric acid itself is used for the esterificatipn, then from 75 to 100% strength by weight, preferably from 85 to 98% strength by weight, of acid is advantageously used (so-called "concentrated sulfuric acid" or "monohydrate"). The esterification can be carried out in a solvent or diluent if one is desired for controlling the reaction, e.g. the evolution of heat. In general, the alcoholic reactant is initially introduced, and the sulfating agent is gradually added with continuous mixing. If complete esterification of the alcohol component is desired, the sulfating agent and the alkanol are used in a molar ratio from 1:1 to 1:1.5, preferably from 1:1 to 1:1.2. Lesser amounts of sulfating agent can be advantageous if mixtures of alkanol alkoxylates according to the invention are used and the intention is to prepare combinations of neutral and anionic surfactants. The esterification is normally carried out at temperatures from room temperature to 85° C., preferably in the range from 45 to 75° C.

In some instances, it may be advantageous to carry out the esterification in a low-boiling water-immiscible solvent and diluent at its boiling point, the water forming during the esterification being distilled off azeotropically.

Instead of sulftric acid of the concentration given above, for the sulfation of the alkanol mixtures according to the invention it is also possible, for example, to use sulfur trioxide, sulfur trioxide complexes, solutions of sulfur trioxide in sulfiric acid ("oleum"), chlorosulfonic acid, sufliryl chloride and also amidosulfonic acid. The reaction conditions are then adapted appropriately.

If sulfur trioxide is used as sulfating agent, then the reaction can also be carried out advantageously in a falling-film reactor in countercurrent, if desired also continuously.

Following esterification, the mixtures are neutralized by adding alkali and, optionally after removal of excess alkali sulfate and any solvent present, are worked up.

The acidic alkanol sulfates and alkanol ether sulfates and salts thereof obtained by sulfation of alkanols and alkanol ethers according to the invention and their mixtures are likewise provided by the present invention.

In an analogous manner, alkanols and alkanol ethers according to the invention and mixtures thereof can also be reacted (phosphated) to give acidic phosphoric esters using phosphating agents.

Suitable phosphating agents are mainly phosphoric acid, polyphosphoric acid and phosphorus pentoxide, but also $POCl_3$ when the remaining acid chloride functions are subsequently hydrolyzed. The phosphation. of alcohols has been described, for example, in Synthesis 1985, pages 449 to 488.

The acidic alkanol phosphates and alkanol ether phosphates obtained by phosphation of alkanols and alkanol ethers according to the invention and their mixtures are also provided by the present invention.

Finally, the use of the alkanol ether mixtures, alkanol glycosides and the acidic sulfates and phosphates of the alkanol mixtures and of the alkanol ether mixtures preparable starting from the olefin mixtures according to the invention as surfactants is also provided by the present invention.

The working examples below illustrate the preparation and use of the surfactants according to the invention.

EXAMPLE 1

Heterogeneously Catalyzed Dimerization of Hexene Isomer Mixtures

A 2.5 l autoclave with rotary stirrer was charged with 200 ml of a catalyst of the following composition:

50% by weight of NiO, 34% by weight of $SiO_2$, 13% by weight of $TiO_2$, 3% by weight of $Al_2O_3$ (conditioned for 24 hours at 160° C. in $N_2$, used as powder).

500 g of 1-hexene and 500 g of dimer propene, consisting of 23% by weight of n-hexenes, 70% by weight of methylpentenes and 7% by weight of dimethylbutenes, were added and reacted for 10 h at 150° C.

The resulting reaction product was worked up by distillation, and a fraction consisting of over 99% by weight of dodecenes was isolated. It has an iso index of 2.1 (4.1 methyl groups/molecule were measured following hydrogenation of the olefin by $^1$H-NMR spectroscopy.), the ratio of aliphatic to olefinic protons is 14.7:1.

EXAMPLE 2

Hydroformylation of the Dodecene Mixture According to the Invention 750 g of the olefin mixture prepared as in Example 1 are hydroformylated with 2.94 g of $Co_2(CO)_8$ at 185° C. and 280 bar of $CO/H_2$ (vol. ratio=1:1) with the addition of 75 g of $H_2O$ in a 2.5 l autoclave with lifter stirrer for 7.5 hours. Cobalt is removed from the reaction product by oxidation using 10% strength by weight acetic acid with the introduction of air at 90° C. The oxo product is hydrogenated in a 2.5 l tubular reactor in trickle mode over a Co/Mo fixed-bed catalyst at 175° C. and a hydrogen pressure of 280 bar with the addition of 10% by weight of water. The alcohol mixture is worked up by distillation. The resulting tridecanol fraction has an OH number of 273 mg of KOH/g. Using $^1$H-NMR spectrography, 3.5 methyl groups/molecule were detected, corresponding to a mean degree of branching of 2.5.

EXAMPLE 3

Fatty Alcohol Ethoxylate Containing 7 mol of Ethylene Oxide 400 g of the alkanol mixture prepared as in Example 2 are introduced with 1.5 g of NaOH into a dry 2 l autoclave. The autoclave contents are heated to 150° C., and 616 g of ethylene oxide are forced into the autoclave under pressure. After all of the ethylene oxide has been introduced into the autoclave, the autoclave is maintained at 150° C. for 30 minutes. Following cooling, the catalyst is neutralized by adding sulfufric acid.

The resulting ethoxylate is a neutral surfactant. It has a cloud point of 72° C., measured in accordance with DIN 53917, 1% strength by weight in 10% strength by weight aqueous butyldiglycol solution. The surface tension of a solution of 1 g/l of the substance in water is 25.8 mN/m, measured in accordance with DIN 53914.

EXAMPLE 4

Fatty Alcohol Ethoxylate Containing 3 mol of Ethylene Oxide 600 g of the alkanol mixture prepared as in Example 2 are introduced with 1.5 g of NaOH into a dry 2 l autoclave. The autoclave contents are heated to 150° C., and 396 g of ethylene oxide are forced into the autoclave under pressure. After all of fin the ethylene oxide has been introduced into the autoclave, the autoclave is maintained at 150° C. for 30 minutes. Following cooling, the catalyst is neutralized by adding sulfuric acid.

The resulting ethoxylate is a neutral surfactant. It has a cloud point of 42.1° C., measured in accordance with DIN 53917, 1% strength by weight in 10% strength by weight aqueous butyldiglycol solution. The surface tension of a solution of 1 g/l of the substance in water is 26.1 mN/m, measured in accordance with DIN 53914.

EXAMPLE 5

Alkyl Phosphate 300 g of the alcohol mixture prepared as in. Example 2 are heated to 60° C. in a stirred vessel under nitrogen, and 125 g of polyphosphoric acid are added slowly thereto. During the addition, the temperature must not exceed 65° C. Toward the end of the addition, the mixture is heated to 70° C. and stirred at this temperature for a further hour.

The resulting product is an anionic surfactant. An aqueous solution of the substance in water has, at a concentration of 1 g/l, a surface tension of 28.4 mN/m, measured in accordance with DIN 53914.

EXAMPLE 6

Alkyl Ether Phosphate 560 g of the fatty alcohol ethoxylate mixture prepared as in Example 4 are heated to 60° C. in a stirred vessel under nitrogen, and 92 g of polyphosphoric acid are added slowly thereto. During the addition, the temperature must not exceed 65° C. Toward the end of the addition, the mixture is heated to 70° C. and stirred at this temperature for a further hour.

The resulting product is an anionic surfactant. An aqueous solution of the substance in water has, at a concentration of 1 g/l, a surface tension of 35.2 mN/m, measured in accordance with DIN 53914.

EXAMPLE 7

Alkyl Sulfate 190 g of the tridecanol mixture prepared as in Exarnple 2 are heated to 60° C. in a stirred vessel under nitrogen, and 98 g of concentrated sulfuric acid are added slowly thereto. During the addition, the temperature must not exceed 65° C. Toward the end of the addition, the mixture is heated to 70° C. and stirred at this temperature for a further hour.

The resulting product is an anionic surfactant. An aqueous solution of the substance in water has, at a concentration of 1 g/l, a surface tension of 28.9 mN/m, measured in accordance with DIN 53914.

EXAMPLE 8

Alkyl Ether Sulfate 480 g of the fatty alcohol ethoxylate mixture prepared as in Example 4 are heated to 60° C. in a stirred vessel under nitrogen, and 146 g of concentrated sulfuric acid are added slowly thereto. During the addition, the temperature must not exceed 65° C. Toward the end of the addition, the mixture is heated to 70° C. and stirred at this temperature for a further hour.

The resulting product is an anionic surfactant. An aqueous solution of the substance in water has, at a concentration of 1 g/l, a surface tension of 34.9 mN/m, measured in accordance with DIN 53914.

We claim:

1. A process comprising:

dimerizing an olefin mixture to form a dimerized product having a degree of branching of between 2.0 and 3.0, and derivatizing the dimerized product to form a mixture of primary alcohols, wherein the olefin mixture comprises from 30 to 80% by weight of linear hexene isomers and at least 60% by weight of hexene isomers overall, and wherein the dimerization is carried out with heterogeneous catalysis.

2. The process as claimed in claim 1, wherein the olefin mixture comprises a hexene isomer mixture comprising dimer propene and linear hexenes in a weight ratio of from 0.3:1 to 1:0.1.

3. The process as claimed in claim 1, wherein dimerizing is carried out with a dimerization catalyst comprising at least one element of subgroup VIII of the Periodic Table and the dimenrzed product comprises less than 10% by weight of compounds which have a structural element of formula I

in which $A^1$ and $A^2$ are aliphatic hydrocarbon radicals.

4. The process as claimed in claim 1, further comprising:

alkoxylating the primary alcohols.

* * * * *